(12) United States Patent
Fehre et al.

(10) Patent No.: US 10,265,035 B2
(45) Date of Patent: Apr. 23, 2019

(54) METHOD AND DEVICE FOR MOTION CONTROL OF A MOBILE MEDICAL DEVICE

(71) Applicant: SIEMENS HEALTHCARE GMBH, Erlangen (DE)

(72) Inventors: Jens Fehre, Hausen (DE); Hans Schweizer, Plattling (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/610,686

(22) Filed: Jun. 1, 2017

(65) Prior Publication Data
US 2017/0347979 A1    Dec. 7, 2017

(30) Foreign Application Priority Data
Jun. 1, 2016    (DE) .................. 10 2016 209 576

(51) Int. Cl.
| | |
|---|---|
| *G05D 1/02* | (2006.01) |
| *A61B 6/10* | (2006.01) |
| *G16H 50/50* | (2018.01) |
| *A61B 6/00* | (2006.01) |
| *G05B 19/402* | (2006.01) |
| *G06F 17/50* | (2006.01) |
| *G06F 19/00* | (2018.01) |

(52) U.S. Cl.
CPC ............ *A61B 6/102* (2013.01); *A61B 6/4405* (2013.01); *A61B 6/4441* (2013.01); *A61B 6/461* (2013.01); *A61B 6/467* (2013.01); *A61B 6/547* (2013.01); *G05B 19/402* (2013.01); *G05D 1/0212* (2013.01); *G05D 1/0274* (2013.01); *G06F 17/5004* (2013.01); *G06F 19/00* (2013.01); *G06F 19/321* (2013.01); *G16H 50/50* (2018.01); *G05B 2219/2652* (2013.01); *G05D 2201/0206* (2013.01)

(58) Field of Classification Search
CPC ..... G05D 1/0212; G05D 1/0274; A61B 6/547
See application file for complete search history.

(56) References Cited

U.S. PATENT DOCUMENTS

2015/0134145 A1\* 5/2015 Lee .................. A61B 19/5244
701/2

FOREIGN PATENT DOCUMENTS

WO    2015068952 A1    5/2015

\* cited by examiner

*Primary Examiner* — Thomas L Dickey
(74) *Attorney, Agent, or Firm* — Laurence Greenberg; Werner Stemer; Ralph Locher

(57) ABSTRACT

Collision-free movement of a mobile medical device, such as a mobile medical imaging device, in a room is controlled via a man-machine interface. A model of the room environment is created and displayed, together an actual position of the medical device. The room model and the actual position are based at least in part on real-time sensor data. A destination position for the medical device is entered, the entered destination position is displayed and a collision-free movement path is generated from the actual position to the destination position. The movement path is displayed in the room model. A movement command relating to the displayed movement path is entered and the medical device is driven along the entered movement path from the actual position to the destination position.

14 Claims, 4 Drawing Sheets

METHOD AND DEVICE FOR MOTION CONTROL OF A MOBILE MEDICAL DEVICE

CROSS-REFERENCE TO RELATED APPLICATION

This application claims the priority, under 35 U.S.C. § 119, of German application DE 10 2016 209 576.5, filed Jun. 1, 2016; the prior application is herewith incorporated by reference in its entirety.

BACKGROUND OF THE INVENTION

Field of the Invention

The invention relates to a method and a device for motion control of a mobile medical device, in particular of a mobile medical imaging device, by way of a man-machine interface.

An increasing trend towards the automation of execution sequences can be observed in the field of medical technology, in particular with medical imaging devices. This applies not only to systems installed as stationary systems, such as, for example, radiography/fluoroscopy systems, but also increasingly to mobile x-ray devices, i.e., those able to be moved about in a room, such as for example C-arm x-ray devices. For this purpose such mobile devices are be equipped with suitable drive platforms, such as omnidirectional wheels or the like for example, and suitable control systems, which make it possible for movement to be automated in the room.

A functionally-capable recognition of the, in some cases dynamically-changing, spatial circumstances at the place of deployment is primarily important for the purpose. Just as important is an associated man-machine interface, which makes possible an intuitive interaction with such a system.

United States published patent application US 2015/0134145 A1 and its counterpart international patent application WO 2015/068952 A1 describe a method for controlling the movement of a medical device. There, a control device receives destination and direction information, such as "right" or "left," from a user by means of a type of remote control. By using sensor data of the environment the control device establishes a collision-free movement path for the medical device and controls the movement process.

SUMMARY OF THE INVENTION

It is accordingly an object of the invention to provide a method and device for motion control which overcomes the above-mentioned and other disadvantages of the heretofore-known devices and methods of this general type and of the present invention to provide a technical improvement, which is characterized by particular ease of operation, for collision-free movement of a mobile medical device in the room.

With the foregoing and other objects in view there is provided, in accordance with the invention, a method for motion control of a mobile medical device, such as a medical imaging device, by way of a man-machine interface. The novel method comprises the following method steps:

generating a room model representing a room environment of the medical device;

displaying the room model and an actual position of the medical device in the room model, wherein the room model and the actual position of the medical device are based, at least in part, on real-time sensor data;

entering a destination position to be arrived at by the medical device and displaying the entered destination position in the room model;

establishing at least one collision-free movement path for a movement of the medical device from the actual position to the destination position and displaying at least one movement path from the actual position to the destination position in the room model; and entering a movement command relating to the displayed movement path and causing a movement of the medical device along a movement path displayed in the room model from the actual position to the destination position.

A core concept of the invention is to equip a mobile medical device, such as a C-arm x-ray device for example, with a man machine interface, which allows a display of the position and an especially intuitive motion control of the medical device. This provides an opportunity for operating the medical device, which in an especially simple manner makes a collision-free movement of a mobile medical device possible and thus makes it possible for the medical device to move around in the room in a manner that can be automated.

The man-machine interface comprises a display device, such as for example a monitor or a display, which provides an operator interface for displaying the spatial conditions in the environment of the medical device, in a similar way to a navigation system. The display device will be activated by an evaluation and control unit, which is preferably designed as a part of the central processing unit of the medical device.

The operator interface can be operated in this case with suitable operating means, wherein this preferably involves operating means integrated into the display device, in particular when a touch-sensitive screen (touch screen) is used, and/or the operating means involves another suitable type of input facility, such as for example a computer mouse. Optionally data eyeglasses can also be used as a display device, if necessary in addition to one of the options given above, in which information, such as for example objects recognized, can be shown in the real image by means of the augmented reality method.

A preferred form of embodiment of the invention relates to a visualization of environmental information (in particular room and object information), room geometries, movement paths and/or collision objects, preferably as a type of physical map, as well as to an intuitive manipulation of a mobile medical device by means of a preferably touch screen based or mouse based man machine interface. The man machine interface in this case preferably serves to operate the device control of the medical device directly. For this purpose the reality is preferably visualized in real time, i.e. the sensor data used for visualization will be acquired cyclically and will be further processed immediately, i.e. without a perceptible delay, but in any event within a narrow time frame.

A mobile medical device in this case is primarily, preferably exclusively, to be understood as a medical device that, by means of suitably drivable movement means, is able to be moved around in the room and in doing so changes its position in the room. The term is used here to distinguish such a device from stationary medical devices, which remain in a single position in the room and are only movable at the location, for example can assume various poses. A typical example of a mobile medical device is an imaging C-arm x-ray device with drivable wheels, which is able to be moved around if required for one position in the room to another position in the room.

In such cases the man-machine interface serves primarily to display to the user at least one route before a fully automatic or semi-automatic movement of the mobile medical device or, where there is provision for this, before a manual movement of the medical device, which will be used later by the medical device. Such cases generally involve a movement of the medical device from a start position, preferably the current actual position of the medical device, into a destination position. Instead of movement path the terms way, route, distance, path, travel path or movement track can also be used.

The travel path to be displayed to the user and if necessary to be selected by the user and/or confirmed by them will preferably be established independently by the medical device. In this case the medical device itself has a suitable processing unit, which will also be referred to below as an evaluation and control unit. This evaluation and control unit is preferably designed as a part of the central processing unit of the medical device. The route can however also be calculated in a processing unit outside of the medical device, for example in a room detection system, which will be explained in greater detail further on in this document.

To establish the movement path, environmental and object information will be needed, in particular information about the room in which the medical device is located, as well as information about the medical device itself. In this case the evaluation and control unit establishes, based on a recognition of a medical device in a monitored room, a risk of collision between the medical device and further objects in the room model and on this basis one or more possible routes for reaching the desired destination position. Suitable path planners as well as collision avoidance algorithms are known from the prior art, in particular from the area of robotics, and will be executed in the evaluation and control unit.

Using the current room and object information and a collision model (model for collision recognition), the evaluation and control unit, by suitable activation of the display device, visualizes the room model as well as the position of the medical device and the route(s). At the same time the drive control of the medical device able to be connected to or connected to the evaluation and control unit, using the current room and object information and a collision model, activates the drive of the medical device. The drive preferably involves an electric-motor drive for a number of omnidirectional wheels of the medical device. In a simple form of embodiment, in which no omnidirectional drive units are used, wheels able to be steered and driven by motors in a classical manner are also conceivable.

The visualization of the movement path primarily serves to confirm the route to the user or enable correction of the route by the user. The user of the man-machine interface should and can decide on the basis of the display of the movement path, whether a specific movement path is to be selected or whether for example an alternate movement path would be more suitable.

If a number of destination positions are available for selection, the option preferably exists for these to be selected and/or confirmed by the user in a different manner, for example by a manual selection with the aid of the man machine interface, e.g. by means of an input device, such as the computer mouse.

The destination position can also involve a position displayed as a preferred position by the evaluation and control unit, such as for example a parking position, which will automatically be added to the list of possible destination positions if corresponding position markings are present in the room and will be recognized automatically.

The destination positions to be arrived at can involve not just parking or operating positions. In other words the invention is not just restricted to moving a medical device from an operating position, e.g. an x-ray position, into a parking position and back again. The destination position can involve an alternate or a further operating position. In other words it is also possible to move the medical device from a first operating position into a second operating position, for example into an operating position with another angulation of the C-arm.

The movement path is preferably visualized within the framework of a presentation of a virtual environment, for which a three dimensional room model will be used. This three dimensional room model and also the collision model, which will be used for evaluating the risk of collisions on the path selected in each case, will be created or updated using that data that emerges from or will be provided by the room detection method described in greater detail later.

Regardless of the fact that the room model and also the collision model will preferably be created and processed using all three room coordinates, the data can be displayed within the framework of the operator interface, in particular the display of the environment and/or the display of the route, preferably optionally three-dimensionally or two dimensionally. In a two-dimensional view there is a an overhead view of the room in which the medical device is located. The three-dimensional, spatial presentation of the environment or of the room, typically of an operating room or the like, is preferably undertaken from the bird's-eye perspective but also from an isometric perspective, for example obliquely from above or from the perspective of the medical device. If a presentation from the perspective of the medical device is used, the presentation is preferably a three-dimensional perspective as seen by a virtual driver. This can specifically be advantageous when a manual propulsion of the medical device is used, since in this way there can be an especially intuitive assignment of the direction of movement of the real system and of the operating elements for motion control represented on the display device.

The man-machine interface then preferably comprises a display device embodied as a type of navigation interface, which is embodied for visualization of the room data and the object data, in particular is embodied for spatial presentation of the actual situation. Preferably such a display device involves a touch screen. As well as the presentation of the room and of the objects located therein, there is also the presentation of the medical device in this case, preferably including the current device setting, such as for example a specific angulation of the C-arm of a C-arm x-ray device.

The medical device is preferably presented in this case with an envelope, which serves as a type of safety area for definition of a collision-free zone around the medical device. The display of such an envelope is especially important for an alternate manual control, in which the medical device will be moved completely or partly without taking account of a route established beforehand, "by eye" so to speak. The envelope not only serves to visualize the medical device. At the same time it preferably forms the outer limits of the medical device used in the collision checking.

Above and beyond this the visualization preferably also comprises the presentation of the path to be covered by the medical device from an actual position into a destination position. Preferably collision warnings will likewise be displayed. These comprise in particular collision warnings in those cases in which a desired destination position cannot be reached without collisions. The collision warning is then already issued during the planning of the movement path or immediately after the planning, but in any event preferably before the beginning of the movement process. Over and above this however collision warnings can also be displayed, which are only produced after the conclusion of the route planning. This relates in particular such cases in which, because of a dynamically changing environment during the movement of the medical device, a collision would take place. Collision warnings generally occur in such cases when the risk of collision exceeds a specific critical value.

The special feature of the man-machine interface employed consists of it mapping a virtual reality, which will be established currently on the basis of real environmental and object data and will be presented practically in real time. The environment as well as the objects that are present within it, including the medical device, are preferably represented symbolically, but can also be represented more or less physically. A physical representation is in particular advantageous in the display of the medical device. In this reality the travel path of the medical device is also represented. The important factor is that the visualization of the route by the man-machine interface not only serves to display an actual state, i.e. the user will be given a visual representation of the actual situation. The visualization simultaneously makes possible the planning of future events, for example possible alternate routes, including a report back to the user about whether they can be implemented. This report can be provided for example by different colored depictions of the routes, for example green for routes that can be implemented and red for routes that are susceptible to collisions. However it is quite particularly important that the visualization makes it possible for the user to exert influence on the behavior of the medical device in the sense of controlling it, and preferably does so with reference to a virtual room model based on real-time information. For this purpose the man-machine interface is linked to the controlling of the medical device, in particular to its drive control. This relates not only to the option of a selection of different routes, the confirmation of a determined route and/or the manual changing of a route, but also to the further, cyclic confirmation of a route once it has been selected during its execution, i.e. while the medical device is traveling on this route, in particular as a type of dead man's switch, and/or the manual abortion of an execution already begun, for example as a result of a collision warning but also as a result of other reasons not communicated by the man machine interface. The dead man's switch in this case is preferably embodied as a part of the input facility, for example as a part of the display device, e.g. as a virtual operating element on the touch screen of a tablet computer used as an input facility. The dead man's switch can however also be realized independently of the display device, for example as a separately embodied classical foot switch pedal able to be actuated while a movement is being carried out.

With this type of inventive motion control a rapid and especially intuitive positioning of the medical device is possible.

The data used for the 3D room model or the collision model involves either exclusively data of mobile sensors, but preferably also additionally data of stationary sensors of a room detection system connected to or able to be connected to the medical device, in more precise terms to the evaluation and control unit.

The preferred method for detection of object and environmental information in a three-dimensional room comprises a recognition or detection of the room geometry. The method preferably operates in real time. That means that the acquired data will be updated cyclically. The acquisition advantageously comprises both a room-related, i.e. generally invariable, static acquisition, and also an object-related, i.e. dynamic acquisition.

In this case, for an acquisition of the room geometry that is as complete as possible, the acquisition is undertaken with the aid of a number of sensors, preferably optical sensors. Typically a multi-sensor network is involved in this case, for example with one or more laser scanners, as well as a number of 3D cameras or with one or more ultrasound sensors as well as a number of 3D cameras. The sensors in this case are connected to or are able to be connected to a processing unit, in which the data will be acquired and processed. The processing unit in this case is either part of the room detection system or part of the medical device. For example the central processing unit of the medical device, in particular the evaluation and control unit, will be used for this. The processing of the data in this case comprises in particular the computation of the room model used by the inventive method and/or of the collision model used by the inventive method.

It is proposed that a mobile medical device, such as, for example, a C arm x-ray device, be equipped with the room detection system. In other words the medical device will be provided with one or advantageously with a number of sensors for spatial position recognition. On the mobile device itself such sensor can e.g. be: laser scanners, 3D depth cameras, normal RGB cameras, preferably arranged around the device with corresponding fish-eye optics and subsequent sharpening of the images for a 360° circular view, capacitive sensors, ultrasound sensors or sensors for magnetic tracking, which operate on the basis of electromagnetic wave propagation. Likewise possible is the use of infrared cameras, as will be used for the stereoscopic tracking method. With the aid of these sensors and corresponding methods for sensor data fusion, the mobile medical device can detect a part of the room and above all its direct environment.

However this is often not sufficient for moving a medical device freely in the room in an automated manner, since the sensors to be used, in particular the sensors of the optical type, cannot see behind blocking objects and thus no complete physical map of the environment is able to be established for route and collision computation. Therefore it is proposed to provide the room in which later the movement of the medical device is to take place, additionally with one or more permanently-installed sensor units. The choice, number and arrangement of these stationary sensors depend, inter alia, on the geometry of the room. Basically the same sensors for room and/or object detection as are able to be used with the mobile device enter into consideration as stationary sensors. Preferably 3D depth cameras will be used as stationary sensors. If infrared cameras are used as stationary sensors, suitable markers are attached to the medical device (and if necessary to other objects to be detected), e.g. marker geometries reflecting actively or passively in the infrared spectrum.

Mobile sensor units are thus a vital presence. These are attached to the mobile medical device itself. Optionally these mobile sensor units will be supplemented by stationary, fixed position sensor units. These stationary sensor units preferably involve immobile sensors, i.e. sensors arranged at one place in the room, which are preferably installed on one or more walls of the room in which the medical device is moving, wherein a wall of a room is also to be understood as a ceiling. The fixed-location sensor units can however also be attached to suitable, preferably immobile items of equipment present in the room, such as for example to cabinets, operating lights, monitor stands or the like.

Sensors used as part of a wall installation are preferably able to be detached from or taken off the wall. This makes it possible to use a set of these sensors in different rooms. In such cases for example adjoining rooms of a hospital or rooms on different floors of the hospital can be involved. For a rapid de-installation of the sensors the sensors can be provided with magnetic holders for example, wherein the corresponding magnetic holders remain on the wall.

A method for placing the sensors in a room comprises either establishing the suitable positions for the wall sensors on the basis of the special features of the room manually, i.e. by hand during the first installation. Or the placement method comprises an automatic dimensioning of the room geometry by means of suitable measurement means, in conjunction with the use of optimization algorithms for sensor placement.

If an initial installation has already been undertaken once in a room and if the optimum sensor positions are not already able to be detected, for example as a result of the magnetic holders left on the wall, then the already known sensor positions for this room can be stored in a data memory able to be read out by the processing unit of the room detection system or in a file and these positions can be displayed to the user for installing the sensors again, for example with the assistance of a projector or of another suitable display means, wherein the projector is preferably attached to the mobile medical device.

Once a room has been measured, or if an already known room is involved then a method for automatically re-recognizing the room is preferably provided. The re-recognition of the room is undertaken in such case for example on the basis of the room geometry and/or on the basis of the recognized positions of the sensors on the walls.

The present invention is generally able to be used with multi axis, mobile medical devices, in particular with mobile medical imaging devices, such as for example with mobile, autonomously-movable C-arm x-ray devices.

The inventive method can be carried out with computer support. The facility suitable for carrying out of the inventive method is able to be realized in part by the provision of a suitable computer program, in particular of a computer program for the central processing unit of the medical device.

With the above and other objects in view there is also provided, in accordance with the invention, a system for motion control of a mobile medical device, the system comprising:

a device configured for creating a model of a room environment of the medical device;

a man-machine interface including a display device and an input device;

the display device being configured for displaying a room model and an actual position of the medical device in the room model, the room model and the actual position of the medical device being based at least in part on sensor data;

the input device enabling an entry of a destination position to be arrived at by the medical device;

the display device being configured for displaying the entered destination position upon entry thereof in the room model and for displaying at least one movement path from the actual position to the destination position in the room model;

the input device enabling an entry of a movement command relating to a displayed movement path; and a computing unit for establishing at least one collision-free movement path from the actual position to the destination position and a drive for moving the medical device along the movement path displayed in the room model from the actual position to the destination position In other words, the novel system, or facility, is specifically embodied for carrying out the method described herein. Preferably the facility comprises at least one data processing or processing unit, embodied for carrying out all steps in accordance with the method described here, which are related to the processing of data. This processing unit preferably involves the central processing unit of the medical device. The data processing unit preferably has a number of function modules, wherein each function module is embodied for carrying out a specific function or a number of specific functions in accordance with the described method. The function modules can involve hardware modules or software modules. In other words the invention, where it relates to the data processing unit, can be realized either in the form of computer hardware or in the form von computer software or as a combination of hardware and software. Where the invention is realized in the form of software, i.e. as a computer program, all the functions described will be realized by computer program instructions when the computer program is executed on a computer with a processor. The computer program instructions are realized in this case in a manner known per se in any given programming language and can be provided to the computer in any given form, for example in the form of data packets, which will be transmitted over a computer network, or in the form of a computer program stored on a disc, a CD-ROM, a flash drive or another data medium.

Other features which are considered as characteristic for the invention are set forth in the appended claims.

Although the invention is illustrated and described herein as embodied in motion control for a mobile medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

The figures of the drawing illustrate the invention schematically and with its major elements. In the figures the same reference characters correspond to structurally or functionally equivalent elements.

DETAILED DESCRIPTION OF THE INVENTION

Figure 1:
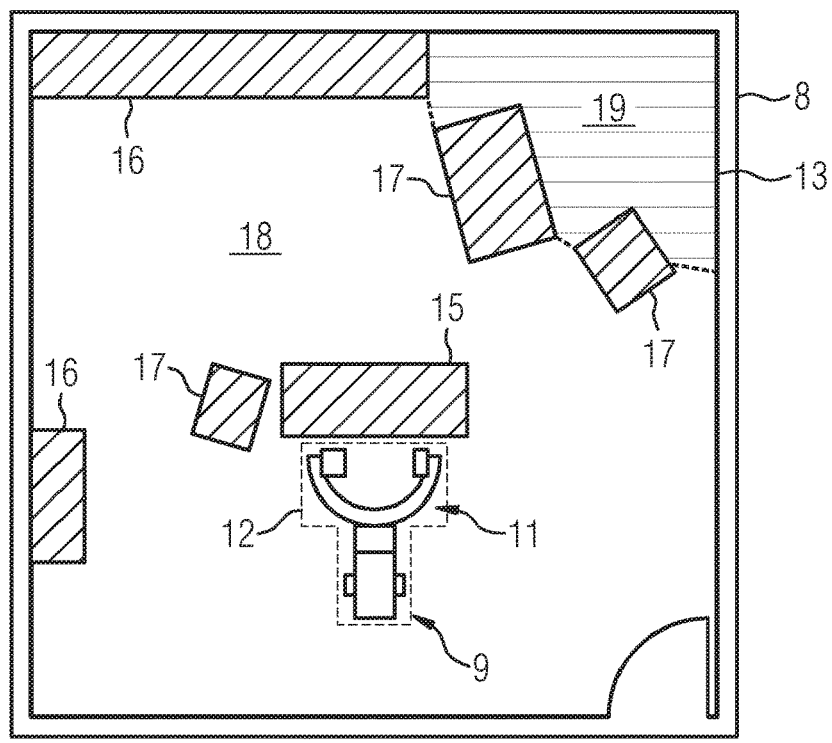
FIG. 1 is a plan view of an exemplary room model mapped by a man machine interface with the position of the C arm x ray device.
Figure 5:
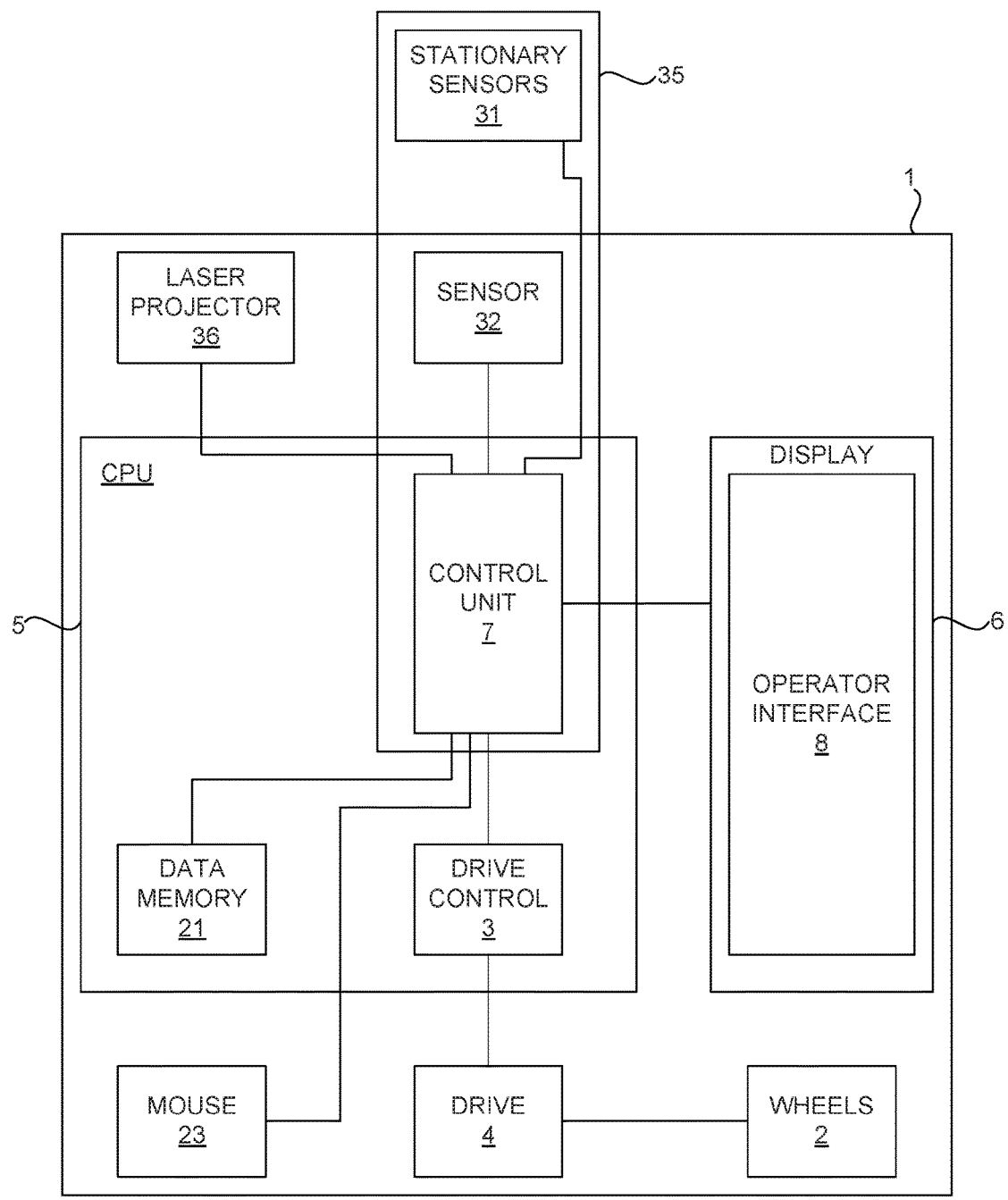
FIG. 5 is a diagram showing the interacting system components.

Referring now to the figures of the drawing in detail and first, particularly, to FIG. 1 and FIG. 5 thereof, there is shown a C-arm x-ray device 1 with a plurality of wheels 2, preferably with three or more wheels, as means of movement. The wheels 2 are preferably able to be driven independently of one another, for example by means of separate drives 4, activated by a drive control 3, in particular electric motor drives 4. In a preferred implementation, the wheels are omnidirectional wheels 2. The drive control 3 is embodied as part of a central processing unit 5 of the x-ray device 1.

The x-ray device 1 comprises a man-machine interface, which has a touch screen 6 as its display device. The touch screen 6 will be activated by an evaluation and control unit 7, which thus controls all displays on the touch screen 6 and also receives all inputs or user interactions. The evaluation and control unit 7 is embodied as part of the central processing unit 5 of the x-ray device 1.

An operator interface 8 is displayed on the touch screen 6. A part of the operator interface 8 is a visualization of the actual position 9 of the x-ray device 1 to be moved. For this purpose a model 11 of the x-ray device 1 will be mapped, which reproduces its current spatial position and location in the room.

FIG. 1 shows a diagram of the model 13 of the operating room 14 as a type of physical map with the model 11 of the x-ray device 1 placed in the correct position. In the figure the model 11 of the x-ray device 1 is shown by way of example in an overhead view with a C-arm angulated by 90°. In the situation shown in FIG. 2 the C-arm of the x-ray device 1 is located in the non-angulated travel position, which is also reflected in the mapped model 11.

In both cases an envelope 12 depicted by dashed lines is shown, which corresponds to the current contour of the x-ray device 1 and will preferably be approximated by one or more rectangles. The surface enclosed by the envelope 12 represents that area in which, with later movements of the x-ray device 1, no contact with other recognized objects or persons is allowed. In a similar way to the graphically represented model 11, this will also be used as part of a collision model in the evaluation and control unit 7, in order to recognize collisions or to avoid them.

The model 11 of the x-ray device 1 will be placed in accordance with its actual spatial position in the room 14, for example an operating room, on the touch screen 6 and will be presented in relation to its environment. In the examples illustrated the x-ray device 1 is mostly located in the vicinity of a patient table 15 and there are further objects located in the operating room 14, such as for example cabinets 16 in fixed locations and mobile medical devices 17, see FIG. 6, wherein, for the sake of simplicity, the same reference characters will be used for the real objects mapped in FIG. 6 and the virtual objects mapped in FIGS. 1 to 4.

The position can be established for example with the aid of optical sensors, such as for example a number of laser scanners and 3D depth cameras and/or stereoscopic navigation cameras. Other sensors such as ultrasound sensors and capacitive proximity sensors can also be included. Furthermore a fusion of the room detection data of a number of independent sensor and/or camera systems is also possible and advantageous, since a direct line of sight of an individual sensor system for monitoring the entire room geometry is very unlikely. Details for the method for room detection preferably used here will be described further on in this document.

As well as the model 11 of the x-ray device 1, further static and dynamic obstacles or objects 15, 16, 17 will be presented as part of the operator interface 8. The non-shaded area 18 in FIG. 1 is in principle able to be reached by the x-ray device 1 without a collision, provided the envelope 12 does not touch any of the objects 15, 16, 17 represented as obstacles, which are represented by oblique-line shading. If there are areas 19 that cannot be reached in principle, these will likewise be drawn on the physical map. In FIG. 1 the area 19 is shown with horizontal-line shading.

The room model 13 will be created by the evaluation and control unit 7, preferably exclusively using current sensor data. In other embodiment variants of the invention, data which has not been currently established by sensors, but which is stored in a file 21 to which the evaluation and control unit 7 has access, in particular for positions and extensions of objects, can additionally be used for the creation of the room model 13.

The floor surface of the room model 13 is divided into the different areas by the evaluation and control unit 7 using a collision model. To this end the evaluation and control unit 7 also serves as a collision computer. The model 11 of the x ray device 1 as well as the room model 13 with the different areas preferably in different colors are presented by the display device 6 of the man-machine interface activated accordingly by the evaluation and control unit 7.

The user can now specify one or more different destination positions 22. This is done with the aid of the operator interface 8 shown by placing the device model 11 at the desired destination position, preferably by moving and/or turning the device model 11 on the touch screen 6 with the fingers to the desired destination position. As an alternative the model can be placed with a computer mouse 23.

If a destination position 22 is not able to be reached as a result of known obstacles, in one form of embodiment of the invention the evaluation and control unit 7 prevents the desired destination position 22 from being entered at the operator interface 8.

If the destination position 22 is basically able to be reached, but not in the current device position, e.g. because an angulation means that the C-arm is too wide for a narrow passage between two objects, the current device position will be stored by the evaluation and control unit 7 and the user will be asked, by means of a suitable interrogation process, whether the x-ray device 1 should assume a more favorable position for the travel process, e.g. by setting the C-arm to the raised position, and whether after the end of the travel movement the old position is to be restored.

Figure 2:
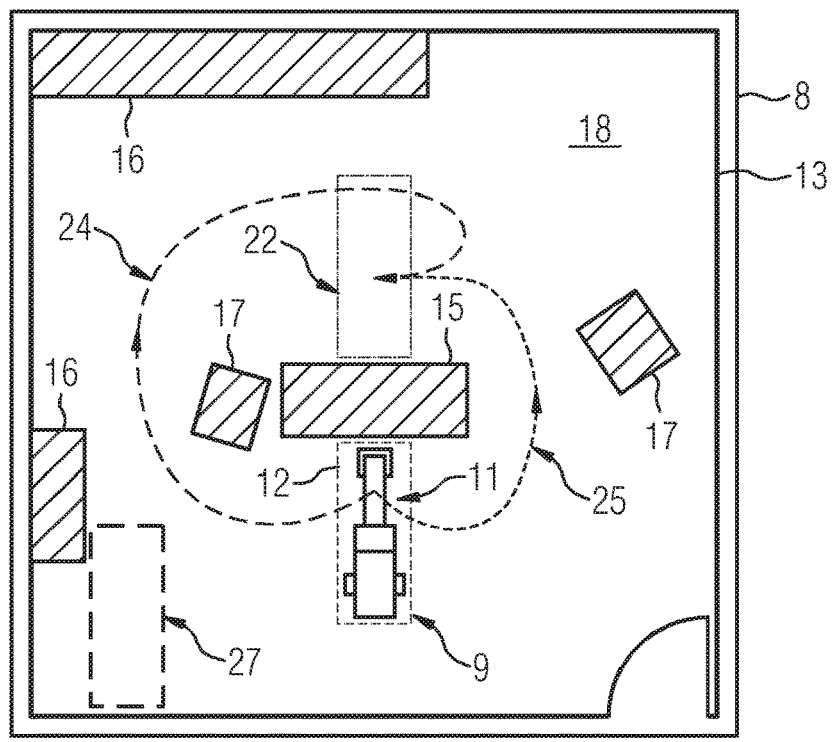
FIG. 2 shows a room model in input mode with destination position specification, suggested route and alternate route as well as parking position.
Figure 3:
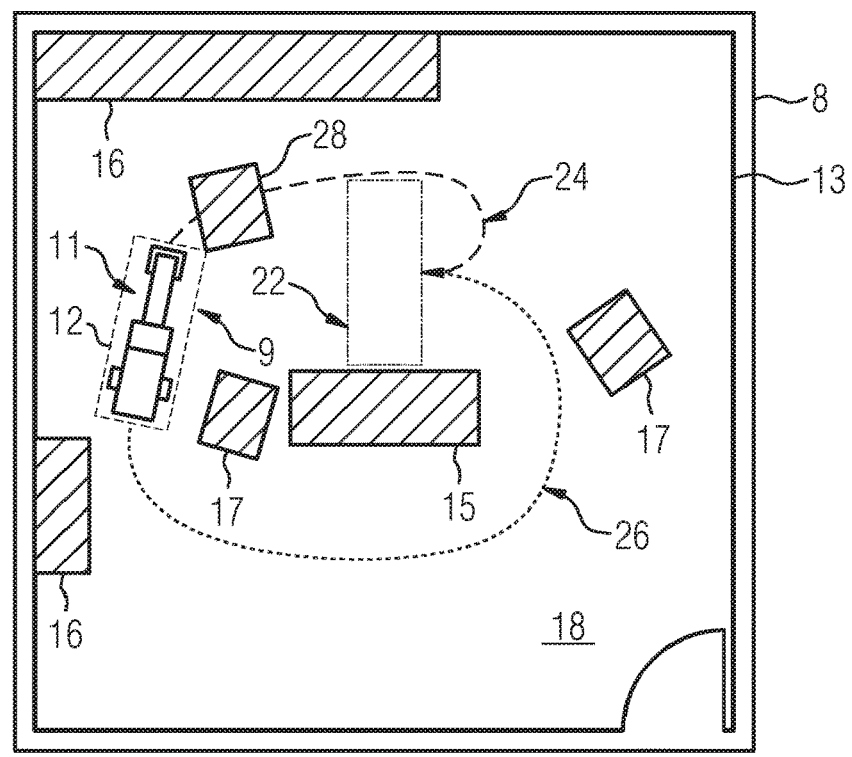
FIG. 3 shows a room model with alternate route proposal when there is a danger of a collision.

If the destination position 22 is able to be reached, it will be accepted and stored by the evaluation and control unit 7 of the x-ray device 1. It is then visible as the new destination position 22 alongside the current actual position 9 of the x ray device 1 in the map depicted as part of the operator interface 8, as is shown in FIG. 2.

Subsequently preferably two options are provided for how the x-ray device 1 can be moved from the actual position 9 to the destination position 22. In an automatic mode the most favorable route 24 computed by the evaluation and control unit 7 will be displayed to the user on the physical map. In this case a time-optimized route can preferably be involved. Such a route proposal is depicted in FIG. 2. The user can confirm this route 24 and have the x-ray device 1 moved with the aid of a suitable, first fail-safe initiation mechanism along this route 24.

The initiation mechanism for initiating the movement command can for example involve a suitable foot switch or any given type of remote control, preferably with a dead man's switch function in each case, or a first failure-safe computer (tablet, PC, smartphone, . . . ). The corresponding processes and facilities for first failure-safe control are known from the prior art. The facility for implementing the initiation mechanism in this case, like the touch screen, has a wired or wireless connection to the evaluation and control unit 7. In the present example the man-machine interface makes the initiation mechanism available via the operator interface 8 presented on the touch screen 6.

In this case the evaluation and control unit 7 looks after the collision recognition, via the drive control 3, for steering and driving of the wheels 2 of the x-ray device 1. The user only has to give the actual movement command. The current actual position 9 and all recognized static and dynamic objects 15, 16, 17 will preferably, both before the actual movement of the x-ray device 1, namely for planning the route 24, and also during the movement of the x-ray device 1, namely for controlling the process of traveling on the route 24, will be updated continuously on the physical map shown as the operator interface 8, i.e. in the room model 13, and in the collision computer.

With the proposed man-machine interface destination positions 22 in the room model 13 can initially be simulated, before they are arrived at a later point in time, when they prove to be usable. If a route predetermined by the evaluation and control unit 7 does not appear as optimal to the user, he can draw in an alternate route 25 in a manual editing mode via the operator interface 8. This can again be done with the fingers or the mouse. The evaluation and control unit 7 checks this alternate route 25 for implement ability, optimizes it in accordance with the computed collision data and likewise presents it in the room model 13 as an alternate route 25, see FIG. 2. The user can now decide which route appears better to him and can select this route before giving the movement command. It is especially advantageous for the display device, here in the form of the touch screen 6, to be able to be released from the x-ray device 1 and to be embodied as a first failure-safe input means for initiating the movement command, so that the movement of the x-ray device 1 can be planned and carried out by the user remotely, for example from an adjacent room.

If the evaluation and control unit 7 recognizes the threat of a collision during the movement of the x-ray device 1 during an automatic approach to the destination position 22 because of changed object positions in the environment of the x-ray device 1, then it displays this situation on the physical map and, where possible, proposes an alternate route 26 automatically calculated previously. At least however an avoidance maneuver is undertaken, in order to move around the obstacle. If avoidance is not possible, the movement of the x ray device 1 will be slowed down via the drive control 3 and, if necessary, stopped or the movement will be continued once the obstacle has removed itself from the route. A corresponding control command will be output by the evaluation and control unit 7 to the drive control 3 of the x-ray device 1. Preferably there is provision for the user to confirm the respective control command. If the command is confirmed by the user, the drive control 3 uses the alternate route 26, in order to move the x-ray device 1 to the predetermined destination or in order to realize one of the other specified options. If the operator does not confirm the command the movement own process will be interrupted in any event.

Preferably it is true to say for each movement process of the mobile x-ray device 1 that there must be an ongoing, in particular cyclic, release by the user available so that a movement process will be begun. Preferably the release must be done manually as a kind of dead man's switch by the user himself and be available to the evaluation and control unit 7. The release can be done for example by a cyclic repetition or confirmation of the movement command.

In the event of the necessary safety requirements, in particular the two-channel initiation, not being able to be implemented with the touch screen 6, in addition to the display device, a further input medium can optionally be provided as part of the man-machine interface, e.g. a foot switch (not shown).

Position specifications for destination positions 22, as described above, can be made by moving and/or rotating the device model 11 in the physical map displayed within the framework of the operator interface 8. As an alternative a user can likewise store a current actual position 9 as the destination position 22, in order to be able to return to this position later. Further destination positions can already be predetermined and stored. For selection of a destination position 22 already present, the evaluation and control unit 7 makes available a selection list and displays this on the touch screen 6. The user can select one of the stored destination positions 22 from this list by means of a selection element, for example via a touch screen functionality or the computer mouse 23. In an advantageous embodiment, when the position is stored, as well as the spatial position, the current C-arm setting will be stored as well, i.e. angulation and orbital angle and vertical lift for example. In this way, on arrival at a stored position, this clinical information relevant for the recording process can likewise be restored.

Furthermore it is also possible to define a parking position 27. This can once again be done by a manual position specification, as described above, but can also be done automatically, in that sensors, for example suitable camera systems, recognize corresponding markings on the floor of the room 14, e.g. strips of reflective tape to identify a parking place. Such a parking position 27 is shown in FIG. 2. The sensors can involve own sensors of the x-ray device 1, such as for example a 3D camera and/or sensors of the room detection system interacting with the x-ray device 1, which will be described below.

The parking position 27 can also be designed as an automatic charging facility, for example in accordance with the induction principle, so that energy stores contained in the x ray device 1 will be charged automatically during the positioning of the x-ray device 1 in the parking position 27. An automatic mechanical coupling of the medical device 1 to a corresponding charging station on reaching the parking position 27 is likewise possible for the case in which no contactless charging is provided.

Since the recognized room geometry is unique as a rule, the method can be used so that the evaluation and control unit 7 remembers all destination positions 22 once created in this room 14, as soon as it recognizes the known room geometry again, thus has identified the room 14. This can be a practical function if the x-ray device 1 will be moved back and forth between a number of operating rooms for example.

Figure 4:
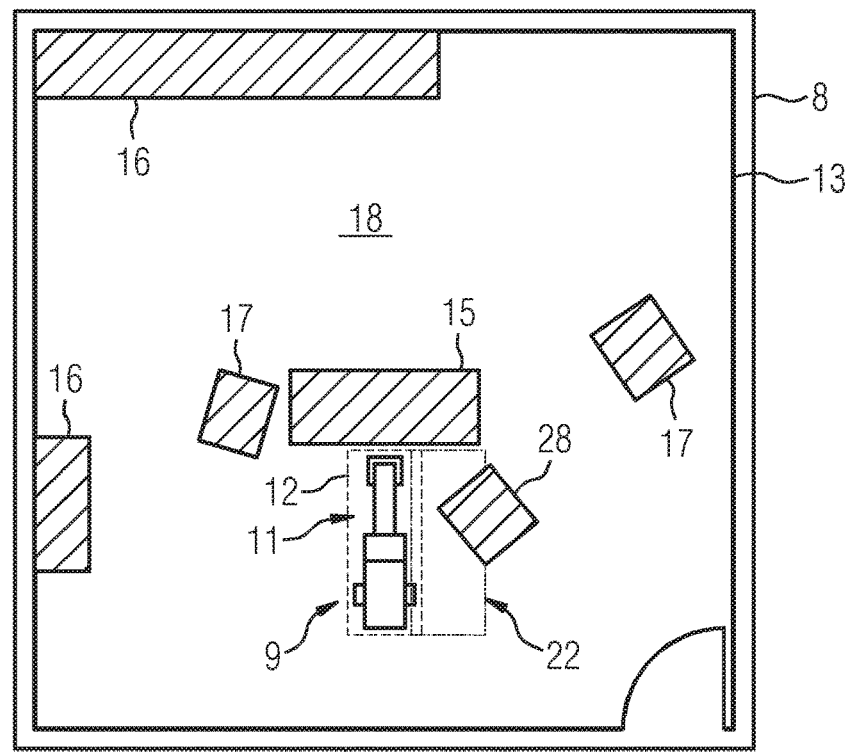
FIG. 4 shows a room model with collision display for planned recording technology.

The physical map principle can also be used for visualization of specific, previously-determined movement patterns. For example such movement patterns can be: a spiral scan (or pseudo spiral scan in the case of a C-arm x-ray device), a movement along a defined curved track to record a number of x ray images, a movement in a projection plane at right angles to a previous recording. For such patterns it is known in advance to the evaluation and control unit 7, more precisely to the collision computer provided by the evaluation and control unit 7, which area of the room the x-ray device 1 must pass through. If there are obstacles there, which would prevent a free movement of the x-ray device 1, the evaluation and control unit 7 can already visualize during the selection of such a function in the physical map, where a collision will take place or which objects 15, 16, 17 the user must remove so that the movement pattern can be carried out. FIG. 4 shows this using the example of a planned, linear displacement of the x-ray device 1 in parallel to the operating table to record a number of x-ray images, which will subsequently be combined into an overall recording. Here the evaluation and control unit 7, on the basis of the data available to it, recognizes an object 28 in the movement area, which must first be moved out of the way by the user, before the parallel travel is released.

The surface areas shown on the touch screen 6 will preferably be shown in color in accordance with their characteristics. Thus for example an area allowing free travel 18 can be shown in green and an inaccessible area 19 can be shown in yellow, while, if there is a danger of a collision, the route 24, 25, 26 and/or an additional warning can be shown in red.

While the actual position display and motion control of the x ray device 1 have been explained in greater detail above, the manner in which the room geometry is acquired will be discussed more fully below.

Figure 6:
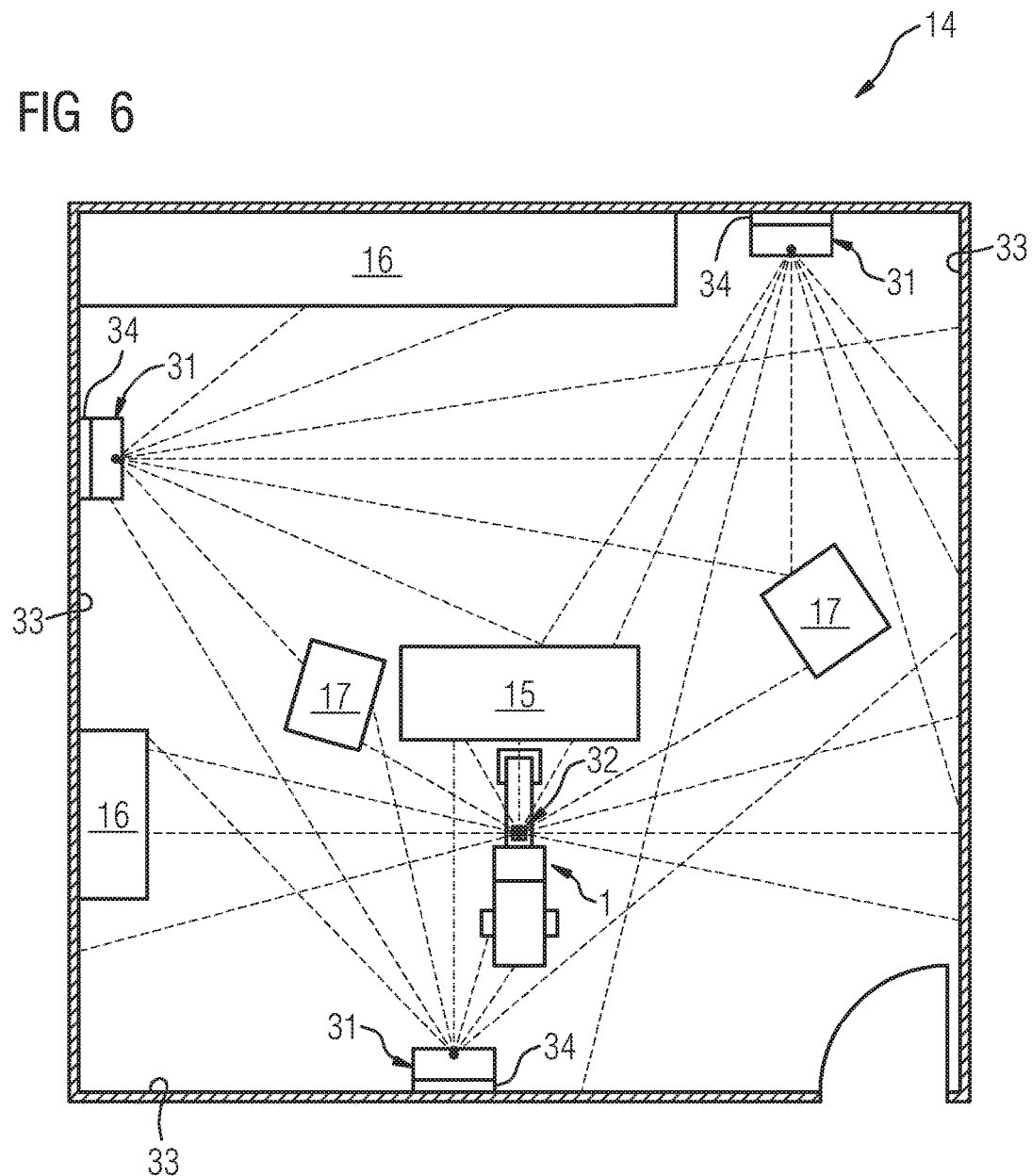
FIG. 6 is a diagram showing an operating room with sensor setup.

FIG. 6 shows a greatly simplified and schematic diagram of a real operating room 14 with a sensor setup. The diagram is similar to the room models 13 shown in FIGS. 1 to 4, as will be displayed by the display device 6 of the man-machine interface, since these room models 13 map the real operating room 14 virtually. The sensor setup for a temporally-continuous volume and object recognition of a typical operating room 14 comprises three stationary 3D cameras 31, actively measuring the distance, and a laser scanner 32 mounted pivotably on the mobile x-ray device 1. The three-dimensional environment detection will be achieved with two-dimensional laser scanners 32 by a pivotable drive of the laser scanners 32, through which the scanning plane of the laser scanner 32 will be moved in the room and as a result the room will be moved in three dimensions.

The advantage of the combination of a number of sensors 31, 32 is that, by the partial redundancy of the volume data, an almost complete, spatial picture of the local circumstances can be acquired, which is of importance for an automated device movement and collision avoidance. In this case there is preferably provision for part areas of the room 14, in which there is a great demand for a precise modeling of the environment, to be acquired once more separately by further sensors, through which the precision of the model of the environment will be increased in these part areas. Such part areas are in particular areas in which an increased activity will be assumed through movement of objects or persons.

The sensors 31, 32 used here can be arranged in any given way in the room 14. In particular they can be arranged at fixed positions in the room 14. However the option also exists of arranging at least a part of the sensors 32 on one or more mobile devices 1 in the room 14. In particular this also enables areas of the environment to be acquired, which in specific positions of the mobile device 1, cannot be seen by sensors 31 arranged at a fixed position, since they are in the shadow of the mobile device 1. The areas acquired by the respective sensors 31, 32 are indicated in FIG. 6 with the aid of symbolic beams that, starting in each case from the center of the sensors 31, 32, pass through an area of the room. It is especially advantageous for the sensors 31 attached to the walls 33 of the room 13 to be designed to allow their removal. For example wall holders 34 permanently attached to the walls 33 can be provided, with which 3D cameras 31 are detachably connected.

Not only the room 14, but also the mobile x-ray device 1 located in the room 14, will be acquired with the sensors 31, 32, wherein the room volume occupied by the x ray device 1 will be specified in the three-dimensional environment model. Subsequently, based on such an identification of a mobile x ray device 1, a risk of collision between the x-ray device 1 and further objects 15, 16, 17 will be established in the room model 13 by the collision processor realized in the evaluation and control unit 7.

The 3D cameras 31 mentioned involve what are known as Time of Flight (TOF) cameras for example, i.e. cameras, which measure distances with a time-of-flight method. 3D cameras of which the method of operation is based on other methods are likewise able to be used. Instead of the 3D depth cameras other distance-measuring acquisition means can be employed as sensors, in order to acquire the area of the environment of the mobile x-ray device 1 in three dimensions. As an alternative to the mobile laser scanner 32, an ultrasound sensor can also be attached to the x-ray device 1 for example.

The stationary sensors 31, here in the example 3D depth cameras, communicate in this case using a wireless method, e.g. WLAN or Bluetooth, with the x-ray device 1. The stationary sensors 31 preferably have an independent energy source, e.g. an accumulator, in order to make entirely cable less operation possible. The stationary sensors 31 deliver the necessary data to the evaluation and control unit 7 located in the x-ray device 1, which merges all sensor data and creates from said data a cyclically updated physical map of the device and room environment, the room model 13. At the same time and for the same purpose the mobile sensor 32, here the laser scanner, communicates with the x-ray device 1. In other words, with computer support, a three-dimensional environment model (room model) 13 will be created. As well as the boundaries (walls) 33 of the room 14, this specifies in particular the volume of the room, which is occupied by objects 15, 16, 17, such as cabinets, tables, other medical devices or also persons.

During the initial commissioning of the mobile x-ray device 1 the best location for attaching the stationary sensor units 31 will either be established in a manual, classical method "by hand." Or in an advanced method the room geometry will be acquired once, for example by means of a portable 3D laser scanner, as is known in the prior art. Subsequently a suitable algorithm in the processing unit of the room detection system 35, which can also involve the central processing unit 5 of the x-ray device 1, computes the optimum number and position of stationary sensor units 31 and shows these positions either on the touch screen 6, to data eyeglasses as an augmented reality display or by means of an optional laser projector 36, which is preferably part of the x-ray device 1, on the walls 33 of the room 14. Magnetic bases can be attached there for example as wall holders 34, for example glued on, to which the autonomous sensor units 31 will be fastened in their turn. The magnetic fastening means that these sensor units 31 are easily detachable and, if the x-ray device 1 is relocated to another room can be easily detached, transported on the x-ray device 1, e.g. in a number of charging cradles, and fastened back in another room onto the wall holders 34 likewise present there.

By means of the stationary sensor units 31 or the recognition of their location in the room 14 or their location in relation to one another, it is further possible for the mobile x-ray system 1 to be able to uniquely identify the room 14 in which the x-ray device 1 is currently located, especially quickly, without a complex acquisition of the entire room geometry being necessary in order to do this.

If no stationary sensor units 31 are obstructed, as an alternative to the active acquisition of the room geometry, there can also be a simple room identification on the basis of recognition features of the room 14 determined. These recognition features can for example involve an arrangement of passive markers (not depicted) in the room, which for example are fastened to the walls 33 of the room 14. The positions of the markers and/or the arrangement of the markers in relation to one another can be acquired by a simple optical system of the mobile x-ray device 1, for example by a camera (not depicted), and be assigned to the room 14. As a further alternative to measuring the room 14 other methods for room identification, such as iBeacons (Bluetooth), infrared transmitters with unique modulation or ultrasound sequences are also conceivable.

The above description is also able to be applied analogously to other medical devices with a number of spatial axes of movement or degrees of freedom, e.g. radiography devices.

Although the invention has been illustrated and described in greater detail by the preferred exemplary embodiment, the invention is not restricted by the disclosed examples and other variations can be derived herefrom by the person skilled in the art, without departing from the scope of protection of the invention.

The following is a summary list of reference numerals and the corresponding structure used in the above description of the invention:

LIST OF REFERENCE CHARACTERS

1 Mobile medical device, C-arm x-ray device
2 Movement means, wheel
3 Drive control
4 Drive
5 Central processing unit
6 Display device, touch screen
7 Evaluation and control unit
8 Operator interface
9 Actual position
11 Model of the x-ray device
12 Envelope
13 Room model, physical map
14 Room, operating room
15 Patient table
16 Cabinet
17 Medical device
18 Reachable area
19 Non-reachable area
21 Data memory, file
22 Destination position
23 Computer mouse
24 Path, route
25 Alternate path, route
26 Collision-avoiding path, route
27 Parking position
28 Collision object
31 Fixed-position sensor, 3D camera
32 Mobile sensor, laser scanner
33 Wall
34 Wall holder, magnetic holder
25 Room detection system
36 Laser projector

The invention claimed is:

1. A method for motion control of a mobile medical device by way of a man-machine interface, the method comprising:

generating a room model representing a room environment of the medical device;

displaying, on a display device, the room model and an actual position of the medical device in the room model, wherein the room model and the actual position of the medical device are based, at least in part, on real-time sensor data;

entering a destination position to be arrived at by the medical device and displaying the entered destination position in the room model;

establishing at least one collision-free movement path for a movement of the medical device from the actual position to the destination position and displaying at least one movement path from the actual position to the destination position in the room model shown on the display device; and entering, by a user, a movement command relating to the displayed movement path and causing a movement of the medical device along a movement path displayed in the room model shown on the display device from the actual position to the destination position, wherein the displayed movement path is displayed on the display device before the movement command is entered.

2. The method according to claim 1, wherein the mobile medical device is a medical imaging device.

3. The method according to claim 1, wherein the generating step comprises creating the room model based on sensor data provided by a room detection system, and wherein the room detection system includes a plurality of sensors mounted to the medical device and/or a plurality of stationary sensors.

4. The method according to claim 1, which comprises creating a collision model based on sensor data provided by a room detection system, the room detection system including a plurality of sensors mounted to the medical device and/or a plurality of stationary sensors, and wherein the generating step comprises establishing the movement path using the collision model.

5. The method according to claim 4, which comprises cyclically updating the collision model and checking for freedom from collisions of the movement path by using the cyclically updated collision model.

6. The method according to claim 1, which comprises continuing a movement of the medical device for as long as a cyclically-repeated release by a user is present.

7. The method according to claim 1, which comprises continuing a movement of the medical device for as long as a freedom from collision of the movement path is given.

8. A system for motion control of a mobile medical device, the system comprising:

a device configured for creating a model of a room environment of the medical device;

a man-machine interface including a display device and an input device;

said display device being configured for displaying a room model and an actual position of the medical device in the room model, the room model and the actual position of the medical device being based at least in part on sensor data;

said input device enabling an entry of a destination position to be arrived at by the medical device;

said display device being configured for displaying the entered destination position upon entry thereof in the room model and for displaying at least one movement path from the actual position to the destination position in the room model;

said input device enabling an entry, by a user, of a movement command relating to a displayed movement path, wherein said display device is configured to display the displayed movement path before the movement command is entered; and a computing unit for establishing at least one collision-free movement path from the actual position to the destination position and a drive for moving the medical device along the movement path displayed in the room model from the actual position to the destination position.

9. The system according to claim 8, wherein the mobile medical device is a medical imaging device.

10. The system according to claim 8, which comprises a device for creating a model for collision recognition.

11. The system according to claim 8, which comprises a device for checking a freedom from collisions of the movement path using a collision model updated cyclically on a basis of sensor data of a room detection system.

12. The system according to claim 8, wherein said man-machine interface comprises a touch screen forming said display device and said input device.

13. The method according to claim 1, which comprises: selecting, by a user, one of a plurality of movement paths shown on the display device as the movement path through which the medical device is moved.

14. The method according to claim 1, which comprises: confirming a movement path shown on the display device by selecting the movement path shown on the display device as the movement path through which the medical device is moved.

* * * * *